(12) United States Patent
Levy

(10) Patent No.: US 7,459,305 B2
(45) Date of Patent: Dec. 2, 2008

(54) INGESTIBLE GASTROINTESTINAL DEVICE

(76) Inventor: Mark M. Levy, 34 Etzion Street, 43 563 RaAnana (IL)

( * ) Notice: Subject to any disclaimer, the term of this patent is extended or adjusted under 35 U.S.C. 154(b) by 672 days.

(21) Appl. No.: 10/766,861

(22) Filed: Jan. 30, 2004

(65) Prior Publication Data

US 2004/0214311 A1 Oct. 28, 2004

Related U.S. Application Data

(63) Continuation-in-part of application No. 10/422,091, filed on Apr. 24, 2003.

(51) Int. Cl.
*C12M 3/00* (2006.01)
(52) U.S. Cl. .................................. 435/287.2
(58) Field of Classification Search ............ 604/57, 604/500; 435/287.2–287.3, 4, 514; 422/56, 422/50

See application file for complete search history.

(56) References Cited

U.S. PATENT DOCUMENTS

| 4,077,407 | A  | 3/1978 | Theeuwes et al. |
| 5,604,531 | A  | 2/1997 | Iddan et al.    |
| 6,168,948 | B1 | 1/2001 | Anderson et al. |
| 6,428,469 | B1 | 8/2002 | Iddan et al.    |

FOREIGN PATENT DOCUMENTS

WO  WO 02/102243 A1 * 12/2002

* cited by examiner

*Primary Examiner*—Ann Y Lam
(74) *Attorney, Agent, or Firm*—Dekel Patent Ltd.; David Klein

(57) ABSTRACT

An ingestible device is provided. The ingestible device comprises a sink mechanism, for generating net influx of at least one constituent-of-interest present in a gastrointestinal tract of an individual, and a confining mechanism for confining the sink mechanism in a predetermined confinement.

38 Claims, 3 Drawing Sheets

INGESTIBLE GASTROINTESTINAL DEVICE

This is a continuation-in-part of U.S. patent application Ser. No. 10/422,091, filed Apr. 24, 2003, the content of which is incorporated herein by reference.

FIELD AND BACKGROUND OF THE INVENTION

The present invention relates to an ingestible device capable of eliminating via removal or conversion, either constructive or destructive conversion, undesirable substances from the body.

For various reasons, including diet, substance use, illness, injury or surgery, patients may require supplementation of their natural body functions in order to remove waste or other products from their blood or gastrointestinal (GI) fluids. Several procedures known for this purpose are dialysis, hemodialysis, hemofiltration and hemodiafiltration. For example, dialysis is used to remove soluble waste and solvent from blood; hemofiltration is used to remove plasma water from blood; and hemodiafiltration is used to remove both unwanted solute (soluble waste) and plasma water from blood.

It is also known that a number of metabolic toxins such as mercaptans, free fatty acids, and conjugated bilirubin and endotoxins are completely bound with proteins in the bloodstream. Because of the size of the molecules and the strong interaction of the components of the protein-toxin complex, it is difficult or impossible to select and remove from blood toxins bound to, for example, albumin by traditional blood purification methods such as hemodialysis. Hemoperfusion is a blood purification method that works in conjunction with activated carbon or iron exchange resins that absorb materials including the protein-bound toxins.

It is well known that individuals that are diagnosed with chronic renal insufficiency can be treated with the aid of dialysis. Substances that are usually eliminated in the urine are removed with the assistance of a filtering device that contains a semi-permeable membrane. However, although dialysis supports life despite complete cessation of renal function, it fails to restore the patient to full functional normality and longevity. Patients affected by chronic uremia, undergoing periodic hemodialysis, frequently develop a clinical picture (also known in the literature as "post-dialytic syndrome") characterized by marked muscular asthenia and a sensation of stupor, particularly evident immediately following dialysis. These conditions, attributed to the loss of carnitine during dialysis, may often last for several hours making difficult, if not impossible, to resume normal activity until these conditions subside.

In addition, during the course of the long term, hemodialysis complications can occur that include chronic accumulation of inorganic phosphate in dialysis patients. Phosphate agents can be administered orally and used as therapeutic agents, which are intended to prevent the reabsorption of food phosphates in the gastrointestinal tract.

Another treatment procedure that has been used is peritoneal dialysis, wherein a sterile saline solution is injected into the peritoneal cavity and remains there for a period of time. The saline solution is separated from the bloodstream by the peritoneum, which is a membrane that is semi-permeable selectively allowing only waste products to diffuse into the saline solution which is then drained out. In addition, osmosis of water through the peritoneum into the saline solution allows the removal of water, excess to overall body needs. This procedure, however, is semi-invasive and carries the risk of infection. Also, such a procedure is not suitable for the removal of a variety of substances, and may not be suitable for all patients.

A disadvantage of various of the above-mentioned treatments is that the biological fluids of the patient have to be transferred from the body, circulated through an exterior treating device, and then returning the biological fluids back to the patient. These treatments are typically done in a medical setting such as a hospital, and require the patient to travel to and from the hospital where the procedure is performed. This process can be time-consuming and disruptive to the normal activity of the daily life of the patient.

Also known are devices which deliver a drug agent to an environment of use. These devices are made with a wall formed of a material that is permeable to an external fluid and substantially impermeable to the beneficial agent. The wall is known to surround a compartment that contains the agent and a passageway through the wall for dispensing the agent.

The intestines (small and large) are recipient of normal local secretions (from the intestine wall) and secretions from exocrine glands of the stomach cells, pancreas and liver (through the bile). That includes hormones, electrolytes and glycoproteins (mucus). On the other hand, efflux and exsorption are processes where the intestine wall secretes into the intestine lumen substances in a way inverted to the intestinal absorption mechanisms (e.g., passive diffusion, facilitated diffusion and specific transport systems), including large molecules and drugs. During exsorption, energy-dependent membrane transporters pump drugs against their concentration gradient out of the cell and back into the intestinal lumen; compared with kidney and liver, little is known about the mechanisms underlying transport into the intestinal lumen.

Intestinal secretion of organic cations was first demonstrated in isolated guinea pig intestinal mucosa. Later studies demonstrated the active secretion of various organic cations into the intestinal lumen. P-glycoprotein, one of membrane transporter pump systems, localized in the intestinal brush-border membrane is involved in the active intestinal secretion of organic cations. In the case of a passive transport mechanism, the exsorption of drugs depends on the concentration gradients between the serosal and mucosal sides. The extent of secretion (exsorption) is determined by numerous factors such as the extent of binding to serum proteins, distribution volume, lipophilicity, pKa and molecular size of drugs, and the blood flow rate in the gut. In addition, changes in pH from ileum to colon affects solubility/dissolution or changes permeability of ionized drugs. Thus, exsorption is more likely for drugs which are characterized by relatively long half lives and low protein binding. Such drugs display unbound blood concentrations higher than the concentration in (gut wall) enterocytes, producing diffusion of drug from blood to enterocytes, followed by diffusion from enterocytes to the intestine lumen. When the lumen concentration is lower than the enterocyte concentration, the "Ka" becomes negative, and exsorption will occur; clearly, if the Ka can reach negative values, it is not constant. This can happen for both oral and IV administered drugs. Re-absorption of the exsorpted drug could cause an increase of its levels at later time points.

Studies have uncovered that specific transport systems such as P-glycoprotein, organic cation and organic anion transporters are involved in active intestinal secretion of drugs such as Immunesuppressives (Cyclosporin, Tacrolimus), Steroids (Aldosterone, Hydrocortisone, dexamethasone), HIV protease inhibitors (Amprenavir, Indinavir, Nelfinavir, Ritonavir, Saquinavir), Cardiac drugs (Digoxin, Digitoxin, Quinidine, Verapamil), Anticancer drugs (Etoposide, Teniposide, Doxorubicin, Paclitaxel, Docetaxel, Vinblastine, Vincristine, Mitoxantrone) and numerous others (Erythromycin, Loperamide, Ondansetron, Fexofenadine).

Abnormal secretions from small and large bowel tumors, pancreas or hepatic system tumors are also produced and secreted into the intestine lumen producing local or systemic effects (following absorption).

Collection of secreted or exsorpted molecules from the gut lumen can lead to reduction or elimination of their local effect on the gut wall. For example, in the case of gastrointestinal hormones, reduction of their concentration or elimination thereof would inhibit cascades that lead to other events or eliminate digestion of certain molecules, thus leading to decrease of absorbable substances in the lumen. These actions would aid in the elimination of toxic levels of substances (endogenous or exogenous), may alter the course of medical conditions or diseases, and may also be used to control levels of drugs which participate in the intestinal exorption process or avoid the absorption of certain nutrients enabling weight control or treatments of various disorders.

In addition, a major function of the intestine is to form a defensive barrier to prevent absorption of harmful substances from the external environment. This protective function of the intestinal mucosa is effected through selective permeability. Evidence indicates that permeability of the intestinal mucosa is increased in most patients with Crohn's disease and in 10% to 20% of their clinically healthy relatives. Permeability is also increased in celiac disease, leaky gut syndrome and in trauma, burns, and as a result of nonsteroidal anti-inflammatory drug treatment.

The major determinant of the rate of intestinal permeability is the opening or closure of the tight junctions between enterocytes in the paracellular space. The tight junctions are narrow belts that circumferentially surround the upper part of the lateral surfaces of the adjacent epithelial cells to create fusion points or "kisses". They are involved in maintaining the cellular polarity and in the establishment of compositionally distinct fluid compartments in the body. Tight junctions are formed by many specific proteins and are connected with the cytoskeleton. The intestinal tight junctions are highly dynamic areas and their permeability can change in response to both external and intracellular stimuli. In fact, the tight junctions play an important role in the regulation of the passive transepithelial movement of molecules. A number of signalling molecules have been implicated in the regulation of tight junction function, including $Ca^{++}$, protein kinase C, G proteins and phospholipase A2 and C. In many intestinal and systemic diseases, changes in intestinal permeability are related to alteration of tight junctions as an expression of intestinal barrier damage. Moreover, permeability of the tight junctions can be modified by bacterial toxins, cytokines, hormones, drugs, trauma and burns.

Zonula occludens toxin derived from *Vibrio cholerae* interacts with a specific intestinal epithelial surface receptor, with subsequent activation of a complex intracellular cascade of events that regulate tight junction permeability.

Zonulin, a novel human protein which is similar to the *Vibrio cholerae* derived Zonula occludens toxin, induces tight junction disassembly and subsequent increase in intestinal permeability in intestinal epithelia. Zonulin likely plays a pivotal role in tight junction regulation during developmental, physiological, and pathological processes, including tissue morphogenesis, movement of fluid, macromolecules and leukocytes between the intestinal lumen and the interstitium, and inflammatory/autoimmune disorders. Zonulin expression is elevated in intestinal tissues during the acute phase of Celiac disease, a clinical condition in which tight junctions are opened and permeability is increased.

Enteric infections have been implicated in the pathogenesis of both food intolerance and autoimmune diseases secondary to the impairment of the intestinal barrier. Small intestines exposed to either pathogenic or nonpathogenic enteric bacteria secrete zonulin. Such secretion is independent of intestinal origin (species) or the virulence of the microorganisms tested; secretion occurrs only on the luminal side of the small-intestinal mucosa, and is followed by a decrease in small-intestinal tissue resistance (transepithelial electrical resistance) which is secondary to the zonulin-induced tight junction disassembly evident from the disengagement of the zonula occludens 1 protein from the tight junctional complex. This zonulin-driven opening of the paracellular pathway may represent a defensive mechanism, which flushes out microorganisms and contributes to the host response against bacterial colonization of the small intestine.

Modulation of intestinal permeability constitute an innovative method of oral drug delivery by enhancing paracellular permeability while modulating epithelial tight junctions. Zonula occludens toxin and human Zonulin are considered candidates for such use. Sodium salts of medium-chain fatty acids, sodium caprate (a dairy product constituent) in particular, have been used as absorption-enhancing agents to promote transmucosal drug absorption. Superporous hydrogel (SPH) and SPH composite (SPHC) also may be used as peptide drug permeation enhancers. Melittin is the major active ingredient in bee venom and has been widely studied for its membrane-fusion property and has been considered as a novel absorption enhancer. Chitosans, other absorption enhancing agents, interact with the cell membrane resulting in a structural reorganization of tight junction-associated proteins which is followed by enhanced transport through the paracellular pathway; the binding and absorption enhancing effects of chitosans on epithelial cells are mediated through their positive charges.

Taking advantage of the new knowledge applied in pharmacology for drug delivery by permeability modulation to increment absorption, exsorption of blood molecules can also be enhanced when using such agents in conjunction with an element that selectively could bind the undesired molecules for further excretion. Also removal of excessive zonulin produced inside the intestine lumen may alter the disease course in many conditions by restoring its defensive barrier function.

A known group of polymers called non-absorbed polymers are designed to operate in the gastrointestinal tract and selectively bind specific target molecules. These polymers are orally administered in capsule or tablet form, pass through the stomach and into the intestines where targeted molecules bind with the polymer, pass through the intestinal tract, and are excreted from the body.

These and other orally administered treatments suffer from many disadvantages. For example, several therapeutic agents which could have been useful in the context of converting gastrointestinal constituents into a non-toxic state, are in fact sensitive to the pH levels characterizing the gastrointestinal environment, and would be destroyed in the gastrointestinal tract, therefore such agents cannot effectively be used. In addition, many therapeutic agents cause damage to one or more organs or tissues of the gastrointestinal tract. The mechanisms for such damage may involve changes in the quality and quantity of mucous, bicarbonate secretion and mucosal blood flow of the gastrointestinal tract. Many agents are weak acids and in the acidic environment of the stomach do not ionize, thus making them more able to penetrate the gastric mucosal barrier and gain entrance into mucosal cells. Once inside mucosal cells, the neutral intracellular pH causes the compounds to ionize. The accumulation of the resulting ions in the cell is believed to interfere with other intracellular stabilizing mechanisms thereby enhancing the possibility of damage. When these agents are given systemically they can produce deep clinically significant ulcers. Once the intestinal mucosa is damaged, bacteria, toxins and allergens normally prevented from penetrating the gastrointestinal system can permeate into the bloodstream, where they are carried into all parts of the body, both triggering and exacerbating symptoms. Also bowel habits may be disturbed producing constipation. Thus, the gain from using such agents is smaller than the damage caused thereby.

There is thus a widely recognized need for, and it would be highly advantageous to have, an ingestible device which is capable of removing or converting undesirable gastrointestinal substances, or metabolites, which is devoid of the above limitations.

SUMMARY OF THE INVENTION

According to one aspect of the present invention there is provided an ingestible device, comprising: (a) a sink mechanism for generating an net influx of at least one constituent-of-interest present in a gastrointestinal tract of an individual; and (b) a confining mechanism for confining the sink mechanism in a predetermined confinement, hence directing the net influx is into the confinement.

According to further features in preferred embodiments of the invention described below, the converting the at least one constituent-of-interest comprises an anabolic process.

According to still further features in the described preferred embodiments the converting the at least one constituent-of-interest comprises a catabolic process.

According to still further features in the described preferred embodiments the device further comprises a substance participating in the anabolic process.

According to still further features in the described preferred embodiments the device further comprises a selective membrane for allowing a preferred influx of the at least one constituent-of-interest.

According to still further features in the described preferred embodiments the device further comprises a power source.

According to still further features in the described preferred embodiments the device further comprises a selective membrane for allowing preferred influx of the at least one constituent-of-interest.

According to still further features in the described preferred embodiments the device further comprises a mixing mechanism for actively mixing a content of the predetermined confinement and/or the surroundings of the device.

According to still further features in the described preferred embodiments the mixing mechanism comprises a heating device.

According to still further features in the described preferred embodiments the mixing mechanism comprises a mechanical mixer and a power source for operating the mixer.

According to still further features in the described preferred embodiments the mixing mechanism comprises a sound wave generator.

According to still further features in the described preferred embodiments the device further comprises a flow generating mechanism for actively generating a flow of gastrointestinal fluids through the predetermined confinement.

According to still further features in the described preferred embodiments the flow generating device is a pump.

According to still further features in the described preferred embodiments the confining mechanism comprises a housing.

According to still further features in the described preferred embodiments the housing is designed and constructed so as to prevent damage to the sink mechanism by constituents of the gastrointestinal tract.

According to still further features in the described preferred embodiments the housing is designed and constructed so as to prevent damage to the gastrointestinal tract by the sink mechanism.

According to still further features in the described preferred embodiments the device further comprises a substance for maintaining a predetermined pH level within the predetermined confinement.

According to still further features in the described preferred embodiments the device is made detectable by at least one detection method for detecting the device in the gastrointestinal tract.

According to still further features in the described preferred embodiments the device further comprises a protective cover made of a biodegradable material, the protective cover being design and constructed to degrade only when arriving to a predetermined location of the gastrointestinal tract.

According to another aspect of the present invention there is provided a method of removing or converting at least one constituent-of-interest present in a gastrointestinal tract of an individual, the method comprising providing the ingestible device of claim 1, and prompting ingestion of the ingestible device, thereby removing or converting the at least one constituent-of-interest.

According to yet another aspect of the present invention there is provided a method of removing or converting at least one constituent-of-interest present in a gastrointestinal tract of an individual, the method, comprising (a) generating net influx of the at least one constituent-of-interest, using a sink mechanism; and (b) confining the sink mechanism and the at least one constituent-of-interest in a predetermined confinement; thereby removing or converting the at least one constituent-of-interest.

According to further features in preferred embodiments of the invention described below, the net influx generated by the sink mechanism is substantially higher than a net influx generated by a concentration difference of the at least one constituent-of-interest devoid of the sink mechanism, the concentration difference being the difference between concentrations of the at least one constituent-of-interest in and out of the predetermined confinement.

According to still further features in the described preferred embodiments the method further comprises accelerating an anabolic process of the constituent-of-interest in the predetermined confinement.

According to still further features in the described preferred embodiments the method further comprises providing a substance for participating in the anabolic process.

According to still further features in the described preferred embodiments the method further comprises accelerating a catabolic process of the constituent-of-interest in the predetermined confinement.

According to still further features in the described preferred embodiments the method further comprises oxidizing or reducing the at least one constituent-of-interest using an oxidation-reduction system.

According to still further features in the described preferred embodiments the method further comprises using a selective membrane for allowing a preferred influx of the at least one constituent-of-interest.

According to still further features in the described preferred embodiments the method further comprises actively mixing a content of the predetermined confinement and/or the surroundings of the device.

According to still further features in the described preferred embodiments the method further comprises maintaining a predetermined pH level within the predetermined confinement.

According to still further features in the described preferred embodiments the method further comprises detecting the device in the gastrointestinal tract by at least one detection method.

According to still further features in the described preferred embodiments the at least one detection method is non-invasive.

According to still further features in the described preferred embodiments the at least one detection method is imaging.

According to still further features in the described preferred embodiments the at least one detection method is selected from the group consisting of x-ray imaging, magnetic resonance imaging, ultrasound imaging, gamma-gamma imaging and automatic tracking.

According to still further features in the described preferred embodiments the sink mechanism is selected from the group consisting of a sink material and a sink device.

According to still further features in the described preferred embodiments the sink material is for absorbing the at least one constituent-of-interest.

According to still further features in the described preferred embodiments the sink material is for converting the at least one constituent-of-interest.

According to still further features in the described preferred embodiments the sink material comprises an oxidant for oxidizing the constituent-of-interest.

According to still further features in the described preferred embodiments the sink device comprises a reductant for reducing the constituent-of-interest.

According to still further features in the described preferred embodiments the sink device is for converting the at least one constituent-of-interest.

According to still further features in the described preferred embodiments the conversion of the at least one constituent-of-interest is selected from the group consisting of chemical conversion, mechanical conversion and electrical conversion of the at least one constituent-of-interest.

According to still further features in the described preferred embodiments the confining mechanism comprises linkers linking among molecules of the sink material, thereby forming a molecular mesh structure.

According to still further features in the described preferred embodiments the sink device comprises an oxidation-reduction system.

According to still further features in the described preferred embodiments the generating the net influx is by absorbing the at least one constituent-of-interest.

According to still further features in the described preferred embodiments the sink material is selected from the group consisting of a high affinity sink material, a low affinity sink material and a combination of a high affinity sink material and a low affinity sink material.

According to still further features in the described preferred embodiments the high affinity sink material is selected from the group consisting of an antibody, whereby the constituent-of-interest is an antigen, a receptor whereby the constituent-of-interest is a ligand, a ligand whereby the constituent-of-interest is a receptor, an enzyme whereby the constituent-of-interest is an inhibitor, an inhibitor whereby the constituent-of-interest is an enzyme and a lectin whereby the constituent-of-interest is a saccharide.

According to still further features in the described preferred embodiments the low affinity sink material is selected from the group consisting of a nutritional fiber, a clay and a resin.

According to still further features in the described preferred embodiments at least a portion of the sink material is attached to a solid phase.

According to still further features in the described preferred embodiments the sink material is water soluble.

According to still further features in the described preferred embodiments the sink material is water non-soluble.

According to still further features in the described preferred embodiments the sink material comprises beads.

According to still further features in the described preferred embodiments the sink material comprises a polymer.

According to still further features in the described preferred embodiments the sink material comprises an inert solid phase to which affinity sink molecules are attached.

According to still further features in the described preferred embodiments the converting the at least one constituent-of-interest is by an anabolic process.

According to still further features in the described preferred embodiments the converting the at least one constituent-of-interest comprises is by a catabolic process.

According to still further features in the described preferred embodiments the sink material is a catalyst.

According to still further features in the described preferred embodiments the catalyst is water soluble.

According to still further features in the described preferred embodiments the catalyst is attached to a solid phase.

According to still further features in the described preferred embodiments the catalyst is an anabolic catalyst for accelerating an anabolic process of the constituent-of-interest in the predetermined confinement.

According to still further features in the described preferred embodiments the catalyst is a catabolic catalyst for accelerating a catabolic process of the constituent-of-interest in the predetermined confinement.

According to still further features in the described preferred embodiments the catabolic catalyst is selected from the group consisting of an esterase, a peptidase, a lipase, a saccharidase, a DNAse and an RNAse.

According to still further features in the described preferred embodiments the anabolic process involves at least two constituents of the gastrointestinal tract.

According to still further features in the described preferred embodiments the accelerating the catabolic process catalyst is by a catabolic catalyst selected from the group consisting of an esterase, a peptidase, a lipase, a saccharidase, a DNAse and an RNAse.

According to still further features in the described preferred embodiments the catalyst is selected from the group consisting of an enzyme and a chemical catalyst.

According to still further features in the described preferred embodiments the sink material is a living organism.

According to still further features in the described preferred embodiments the living organism is selected from the group consisting of a bacterium, a unicellular parasite, a multicellular parasite and a fungus.

According to still further features in the described preferred embodiments the fungus is a yeast.

According to still further features in the described preferred embodiments the sink device is an electrical sink device.

According to still further features in the described preferred embodiments the oxidation-reduction system comprises electrodes and a power source.

According to still further features in the described preferred embodiments the mixing is by a heating device.

According to still further features in the described preferred embodiments the mixing is by a mechanical mixer and a power source for operating the mixer.

According to still further features in the described preferred embodiments the mixing is by a sound wave generator.

According to still further features in the described preferred embodiments the method further comprises actively generating a flow of gastrointestinal fluids through the predetermined confinement.

According to still further features in the described preferred embodiments the generating flow is by a pump.

According to still further features in the described preferred embodiments the confining is by a housing.

According to still further features in the described preferred embodiments the housing is composed of a bioresistant material.

According to still further features in the described preferred embodiments the confining is by linkers linking among molecules of the sink material, thereby forming a molecular mesh structure.

According to still further features in the described preferred embodiments the housing is configured for expanding and/or contracting.

According to still further features in the described preferred embodiments the at least one constituent-of-interest is selected from the group consisting of a toxin, creatinine, uric acid, a hepatic toxic metabolite, alcohol, an alcohol metabolite, an electrolyte, a therapeutic or a medicinal agent, a detergent, a renal metabolite, a poisonous substance, a nutritional substance, a biochemical compound and a heavy metal.

The present invention successfully addresses the shortcomings of the presently known configurations by providing a device which can be used for removing or converting a wide range of substances from GI fluid or blood circulation surrounding the GI tract.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1A:
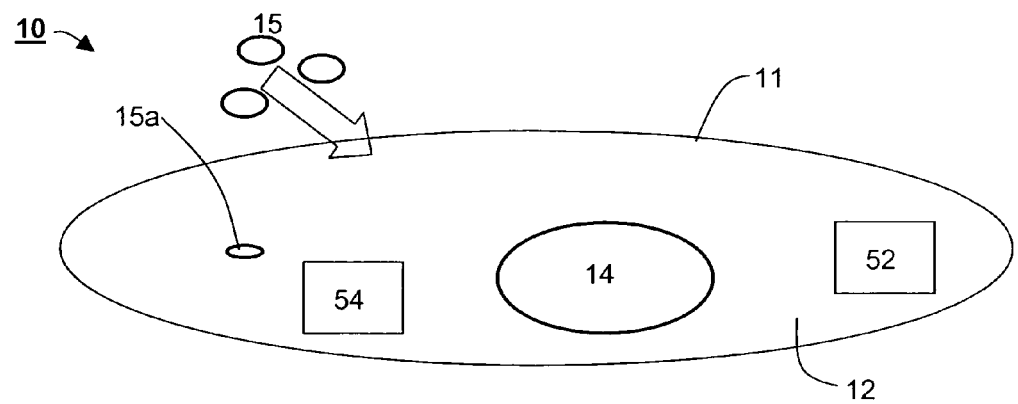
FIG. 1a is a schematic cross-sectional view of an ingestible device having a sink mechanism according to a preferred embodiment of the present invention.

The present invention is of an ingestible device which can be utilized to eliminate via removal and/or conversion, either constructive, e.g., anabolic, or destructive, e.g., catabolic, unwanted substances from gastrointestinal fluids and/or blood circulation surrounding the gastrointestinal tract. Specifically, the present invention can be used to treat individuals having gastrointestinal tract disorders caused by, for example, toxins or other molecules and individuals suffering from other ailments by (i) removing such molecules from the gastrointestinal fluids and/or the blood circulation surrounding the gastrointestinal tract; or (ii) converting such molecules into non-toxic substances.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The gastrointestinal (GI) or digestive tract, also referred to as the alimentary canal, is the system of organs within animals which ingests, digests, and egests food, and in the process, extracts energy and nutrients. The gastrointestinal tract is also a site to numerous disorders and pathologies which affect the normal functioning of this group of organs and other organs in the body. Thus, an optimally functioning gastrointestinal tract is vital for the well being and long term health of both humans and animals.

Although numerous medicaments and various treatment regimens are targeted at pathologies and disorders of the gastrointestinal tract, few examples of agents which are capable of efficiently facilitating removal or conversion of gastrointestinal constituents which participate in, or result from, such pathologies and disorders exist in the art.

The need for a device, which can efficiently remove or convert gastrointestinal constituents and thus treat gastrointestinal disorders and pathologies as well as help balance the levels of nutrients which are absorbed by the blood stream from the gastrointestinal tract, and balance the level of certain molecules that flood throughout the body and hence are present in the gastrointestinal tract, has led the present inventor to devise an ingestible device which can be adapted for efficiently removing a wide array of gastrointestinal constituents.

Thus, according to one aspect of the present invention there is provided an ingestible device which can be utilized to remove or convert at least one constituent-of-interest present in the GI tract, referred to herein as device 10. As used herein, the term "constituent-of-interest" when used in context with gastrointestinal tract refers to a material present in gastrointestinal fluids or in the blood circulating around the gastrointestinal tract (e.g., within the mucosal layer of intestines). Such constituents may be a small molecule, a macromolecule or a pathogenic organism.

As further detailed hereinafter and in the Examples section that follows, device 10 is designed for removing or converting any one of various substances from the blood circulating around the gastrointestinal tract and the fluids present within the gastrointestinal tract. The rich vascular network and length of the gastrointestinal tract provides device 10 with a long dwell time and thus efficient contact between device 10 and the gastrointestinal content as well as the capillary-rich bowel mucosa. The removal of blood or gastrointestinal fluid constituents substantially produces the inverse effect of physiological gastrointestinal absorption.

Generally, device 10 may remove or convert any undesirable constituent present in the gastrointestinal fluid or the blood circulating around the gastrointestinal tract. Specific examples include, without limitation, creatinine, urea, uric acid, hepatic toxic metabolites, unwanted electrolytes, toxins, heavy metals, alcohol, alcohol metabolites, drugs, glucose, fats and any food breakdown products or ingredients which may be irritating to specific individuals (e.g., lactose, gluten or gliadin).

Before providing a further detailed description of device 10, in accordance with the present invention, attention will be given to the advantages and potential applications offered thereby.

Hence, device 10 may be used for many purposes, alternatively or in combination. For example, in one embodiment, device 10 facilitates the binding of substances which result from the breakdown of ingested foodstuff consumed in excess, including, without limiting alcohol, sugars and fats. In such cases, device 10 serves as a diet supplement which can be ingested prior to, during or shortly after eating.

In another embodiment, device 10 may be used for treating diseases or disorders (e.g., gastrointestinal disorders) by removing constituent-of-interest from the gastrointestinal fluid or blood of mucosal capillaries. Removal of such blood constituents can be utilized to treat hepatic or renal insufficiency or other problems associated with high concentration of certain materials in the body, such as diabetes, high bilirubin, etc.

In an additional embodiment, device 10 may be used to avoid possible undesired or over-absorption of substances which are present in food.

Under normal conditions, the absorption of nutrients from the gastrointestinal tract to the blood stream is done through the capillary network. Thus, device 10 can also be used to prevent certain materials from entering the bloodstream through this network, effectively providing a dialysis-type function.

For example, the ingestion of a plurality of devices like device 10 can be used to substantially reduce the blood concentration of an undesirable substance, such as glucose, urea, uric acid, ions and the like without dialysis and/or in a short amount of time as compared to other treatment procedures. In one such conventional treatment, retention enemas using Kayexalate resin is used to lower potassium levels within the body. Kayexalate, a form of sodium polystyrene sulfanate, is a cation-exchange resin prepared in the sodium phase, and lowers serum potassium within the blood. Although effective, such treatment may take hours to days and it has been found that treatment with this drug alone may be insufficient to rapidly correct sever hyperkalemia for example. Using the device of the present invention, the treatment of such a condition may utilize one or more of the devices of the present invention configured capable of continuous removing potassium from the body in an effective and efficient manner.

In cases of oral poisoning, by, for example, bacteria, ethylenglycol, etc., the device of the present invention can be used to remove the toxin and/or convert the toxin into a non-toxic, innocuous substance.

Thus, as should be evident, the removal or conversion via constructive or destructive pathways of a variety of substances from body fluids within the gastrointestinal tract using one or more devices like device 10 may provide an alternative to conventional treatments for a variety of conditions.

Referring now to the drawings, FIG. 1a is a schematic illustration of device 10, which, in its simplest form, comprises a sink mechanism 14, capable of generating net influx of constituent-of-interest 15, and a confining mechanism 11 for confining sink mechanism 14 in a predetermined confinement 12. As further described hereinunder, confining mechanism 11 and confinement 12 are designed and configured so as to facilitate collection and/or conversion of constituent-of-interest 15, hence elimination thereof from the gastrointestinal tract. As some substances, such as urea, flood the body, device 10 of the present invention can be used to systemically eliminate substances such as urea from the body.

As used herein the term "sink mechanism" refers to any molecule, compound, substance, aggregate of substances or device capable of absorbing and/or of converting the constituent-of-interest, so as to act as a functional sink in inducing a flux of the constituent-of-interest towards the sink mechanism.

The term "sink" is frequently used in the art of life sciences to describe models explaining directional gradients, wherein the direction of the gradient is said to be between a source and a sink. In context of the present invention, the source of the constituent-of-interest is the body, the gastrointestinal track in particular, whereby the sink is device 10, having therein sink mechanism 14.

Hence, a particular feature of the present invention is the source-sink relation between device 10 and the body, the gastrointestinal fluid in particular, which is preferably characterized by continues net influx of the constituent-of-interest from the source (e.g., the gastrointestinal fluids) to the sink (i.e., device 10 containing sink mechanism 14).

For the purpose of better understanding the present invention, following is an introductory description of the difference between net influx caused by a sink mechanism and a diffusion characterizing a tendency of any system to arrive to equilibrium.

Hence, an important principle in thermodynamics is the tendency of a system to extremize various thermodynamic functions, which are expressed in terms of the thermal variables of a system, and are often related to one another via a simple Legendre transformation. A variation in the particle number is conjugated to a thermodynamic quantity, called chemical potential. In systems in which the particle number is changed through the boundary of a device (i.e., non-isolated systems), the chemical potential is related to the change in a particular thermodynamic function (e.g., entropy, free energy, etc.). Two systems in which particles are allowed to move from one system to the other tend over time to equate their chemical potentials. The flux of particles between the systems is proportional to the difference between the particle concentrations of the systems. When the chemical potentials are equal, the systems are in equilibrium, there is no difference between the particle concentrations and the net flux from one system to the other is suppressed (although such systems still exchange particles, statistically, for each system, the number of incoming particles equals the number of outgoing particles, hence the suppression of the net flux).

In contrast, if one system is a source or reservoir and the other system is a sink, the net influx from the source to the sink is determined by the ability of the sink to dynamically change the chemical potential of its immediate surrounding, hence to maintain a net flux from the source or reservoir to the sink, which is substantially higher than the net flux that would have been generated had the sink been absent. In other words, the sink is a mechanism, which continuously reduces the concentration of a certain type of molecule in its immediate surrounding, continuously keeps a sufficient concentration difference between the source or reservoir and the sink.

For example, consider two solutions, $S_1$ and $S_2$, separated by a separator permeable to a molecule of type A, so that, initially, the concentration of A in $S_1$ is larger than the concentration of A in $S_2$. Due to the initial concentration difference, the number of A molecules outgoing from $S_1$ and incoming to $S_2$ is larger than the number of A molecules outgoing from $S_2$ and incoming to $S_1$. Thus, $S_2$ experiences a net influx, $F_A$, of molecule A. As a result, the net number of the dissolved A molecules in $S_2$ increases and the difference, D, between the concentrations of A in $S_1$ and $S_2$ decreases. Being proportional to D, the influx, $F_A$, survives only as long as D does not vanish. In other words, $F_A$ is a decaying function of time.

Consider in contrast, that a sink which continuously removes A from $S_2$ is placed in $S_2$. Such sink may be, for example, a solid phase with a large number of binding sites to which molecules of type A can bound, so that A transforms from its liquid state in $S_2$ to a solid state on the structure. In this case, the above mentioned growth of the concentration of the dissolved A molecules in $S_2$ is tamed by the sink. Depending on the surface area of the sink (e.g., the number of vacant binding sites thereof) the concentration difference, D, can be a non-decreasing function, so that $F_A$ is maintained as long as there are vacant binding sites on the structure. More generally, $F_A$ is maintained as long as the sink is operative.

One ordinarily skilled in the art would appreciate that, although initially the net influx in the above two examples may be same, over time, the sink mechanism generates conditions for a significantly higher influx compared to the first example, where there is no sink. As a result, the total net number of A molecules entering $S_2$, is increased.

Thus, according to a preferred embodiment of the present invention the net influx generated by sink mechanism 14 is substantially higher than a net influx generated by concentration difference devoid of sink mechanism 14 as further detailed hereinabove. This can be done by: (i) binding of constituent 15, so as to reduce the concentration of the dissolved or dispersed constituent as exemplified hereinabove, and/or (ii) converting the molecular structure of constituent 15, so as to produce a different substance in confinement 12, thereby to tame the growth of the concentration of constituent 15 therein. In addition, when constituent 15 is charged, sink mechanism 14 can mask or convert its charge, hence allowing the net influx to continue.

According to a preferred embodiment of the present invention, sink mechanism 14 may be either a material or a device.

Sink mechanism 14 can also be in the form of a plurality of sink materials and/or devices, each designed or selected to absorb or convert a particular constituent-of-interest. This embodiment is particularly useful when there is more than one type of constituent-of-interest to be eliminated from the body, or when it is desired to employ several conversion processes (either in a parallel or in a serial fashion). The number of sink materials and/or devices which are included in sink mechanism 14 is not limited. The different sink materials and/or devices may also be confined in different compartments of confinement 12, so as to avoid undesired interactions between the different sink materials, devices constituents and/or converted products derived therefrom. A multi compartment device is further described hereinafter with reference to FIG. 6.

In an embodiment of the present invention in which sink mechanism 14 is a sink material, the material may be either water soluble or water non-soluble, and it is selected so as to absorb via high or low affinity binding and/or chemically or enzymatically convert constituent 15. An absorbing sink material preferably has an affinity and specificity to constituent 15, which affinity and specificity can be low affinity and specificity or high affinity and specificity. Sink mechanism 14 may also be a combination of one or more sink materials of which some have high affinity and some low affinity to constituent 15.

The type of sink material, of course, depends on the type of constituent-of-interest to be eliminated from the body. Many pairs of substances are known to have high mutual affinity. For example, antibodies are known to have high affinity to antigens. Hence, according to a preferred embodiment of the present invention, if the constituent-of-interest is an antigen and the sink material is its specific antibody. More representative examples of pairs of substances with high affinity include without limitation, receptor-ligand, enzyme-inhibitor or enzyme-substrate and lectin-saccharide or polysaccharide.

It is appreciated that in any of the above pairs or other pairs having mutual affinity, if one member of the pair is to be eliminated from the body, the other member of the pair may be used as a sink material in accordance with the present invention.

Representative examples of low affinity sink materials include without limitation, nutritional fibers for expelling fats and various resins for expelling positive or negative ions.

Following are preferred configurations of a sink mechanism 14, in the embodiments in which a sink material (e.g., a polymer) is employed.

Figure 2A:
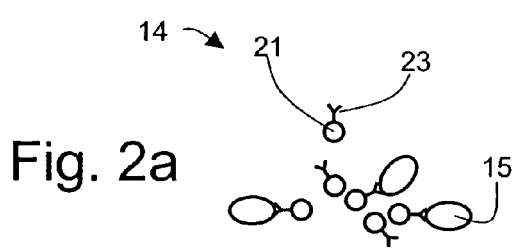
FIGS. 2a-c are schematic illustrations of a sink mechanism, according to a preferred embodiment of the present invention.
Figure 2B:
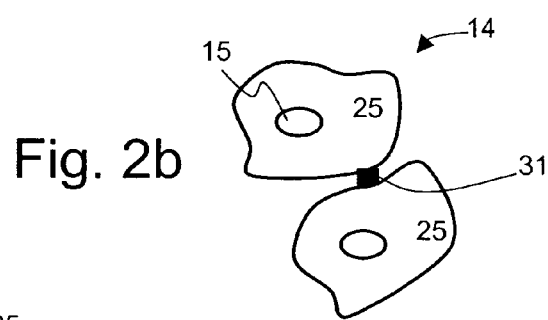
Figure 2C:
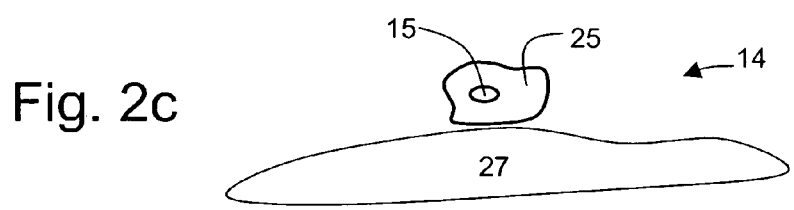

Reference is now made to FIGS. 2a-c which provides schematic illustrations of sink mechanism 14, according to preferred embodiments of the present invention. FIG. 2a shows one embodiment, in which the sink material comprises a plurality of beads 21 having an affinity moiety 23, having affinity to constituent 15, bound or inherent thereto, thereby capable of selectively binding constituent 15. FIGS. 2b-c show another embodiment, in which the sink material comprises a molecule 25 capable of absorbing constituent 15.

It is appreciated that the sink material may include submicroscopic size moieties (for example, an antibody or a receptor). In such cases, according to a preferred embodiment of the present invention, the sink material further comprises an inert solid phase 27 to which the moieties are attached, so as to facilitate accumulation of the sink material within device 10. Suitable chemical linkers can be used to covalently attach the moieties to the solid phase.

It will however be appreciated that submicroscopic size moieties can serve as a sink material according to the present invention also when in solution.

In other cases the sink material is macroscopic in nature and is a solid phase in itself, such as in the case of ion exchange resins.

According to a preferred embodiment of the present invention, sink mechanism 14 may be confined in confinement 12 by more than one way. In one embodiment, confining mechanism 11 is solid phase 27 to which the sink material is attached. In another embodiment, confining mechanism 11 comprises linkers 31 linking molecules 25 of sink mechanism 14. Yet, in other embodiments confining mechanism 11 comprises a chamber including a membrane so selected and constructed so as to confine sink material 14 therein.

As stated, the sink material can generate a net influx into confinement 12 by converting constituent 15. Such conversion may be constructive, e.g., catabolic, or destructive, e.g., anabolic. For example, the sink material may be a catalyst, such as an enzyme or a chemical catalyst, which accelerate a chemical reaction converting the constituent-of-interest. In this embodiment, the catalyst is preferably water soluble or bound to a solid phase, so as to optimize its interaction with constituent 15. As stated, the sink material may convert constituent 15 either by an anabolic process or by a catabolic process.

Specifically, for anabolic processes, the sink material accelerate a process in which new molecules are synthesized from constituent 15 or a portion thereof, preferably so as to form larger molecules (e.g., conjugates or polymers). Because large molecules are less likely to escape from confinement 12, this embodiment is particularly useful in cases where constituent 15, removed from the blood stream and/or gastrointestinal fluids, is to be retained within device 10, so as to be ultimately expelled from the body through normal peristaltic motion of the gastrointestinal tract. In this embodiment, confining mechanism 11 is preferably a housing, which may be partially or fully constructed of a porous material, designed to allow passage-in of certain fluidic constituents, so as to act as a membrane or a unilateral membrane in accordance with the invention.

As used herein, the term "membrane" refers to a structure which allows the passage of predetermined fluidic constituents, while preventing the transmission of other constituents therethrough.

As used herein, the phrase "unilateral membrane" refers to a structure which allows net influx but prevents efflux of predetermined fluidic constituents.

In some case, on the other hand, the synthesized molecule is not or less harmful to the organism or may not be able to be absorbed and hence can be allowed to subsequently diffuse out of device 10. For example constituent 15 may be a toxic material which is first converted by device 10 to a non-toxic material and thereafter returns to the body of the subject.

There are several situations in which the anabolic process is preferred. In one situation, the anabolic process involves two or more constituents-of-interest of the gastrointestinal tract. In another situation, one constituent is not harmful to the gastrointestinal tract, but yet can be sacrificed to participate in a synthesis with the harmful constituent-of-interest. In a third situation, the anabolic process involves one constituent-of-interest of the gastrointestinal tract and an additional substance, present in confinement 12 for the purpose of participating in the anabolic process.

In a catabolic process, the sink material degrades constituent 15 to provide one or more remnants 15a. This embodiment may be useful, for example, when constituent 15 may be degraded into non-toxic remnants. One ordinarily skilled in the art would appreciate that such non-toxic remnants may be allowed to diffuse out of device 10 into the gastrointestinal fluids. Representative examples of sink material useable in context of this embodiment of the present invention include, without limitation an esterase, a peptidase, a lipase, a lactase, a diastase, a pancreatinase, a saccharidase, a DNAse and an RNAse, each of which can be in a disolved state of bound to a solid phase. The utilization of enzyme immobilization technology, like with calcium alginate beads or other techniques broadens the spectrum of applications.

Another type of conversion of the constituent-of-interest, according to an embodiment of the present invention, is by oxidation-reduction. Specifically, if the sink material comprises a molecule that donates electrons (reductant), the conversion of the constituent-of-interest is by reduction. Examples of undesired materials which can be converted by reduction include cooper, lithium, sodium, potassium. If the sink material comprises molecule that accepts electrons (oxidants), the conversion of the constituent-of-interest is by oxidation. Examples of undesired GI constituents which can be converted via oxidation include ammonia, alcohol, glucose, iron, sulfur, fluoride, creatinine. Conversion by an oxidation-reduction reaction can also be accomplished by a sink device, as is further detailed hereinunder.

One ordinarily skilled in the art will appreciate that conversion by an oxidation-reduction reaction is a somewhat less selective process than conversion by anabolic or catabolic catalysts, which can be specifically tailored for the type of constituents that are to be eliminated. Thus, according to a presently preferred embodiment of the invention, device 10 further comprises a selective membrane for allowing or facilitating a preferred influx of the constituent-of-interest. The advantage of using a selective membrane in this embodiment is that the conversion by the oxidation-reduction reaction is enacted preferably on the desired constituent-of-interest, as other constituents of the gastrointestinal tract are prevented from entering confinement 12.

Conversion of the constituent-of-interest can also be accomplished by living organisms, such as, but not limited to, bacteria, parasites (unicellular or multicellular) and fungi (e.g., yeasts). For example, bacteria like lactobacillus, acidophilus consume waste by producing enzymes. These enzymes can convert the constituent-of-interest, as further detailed hereinabove. Similarly to the above conversion by an oxidation-reduction reaction, as living organisms may produce more than one enzyme (hence being less specific in this context), a selective membrane may be used to specify the constituent(s) which is to be converted.

One of ordinarily skill in the art would appreciate that any of the above examples can generate a sufficient net influx of constituent 15 into confinement 12 and preferably to generate condensation of constituent 15 therein. It is to be understood, that although there is a continuous net influx of constituent 15 into confinement 12, the scope of the present invention also include situations in which the net influx is eventually terminated, e.g., when all the binding sites are occupied, and there is no more taming of the concentration growth in confinement 12. Even in such cases, it is appreciated that the total net amount of constituent-of-interest entering confinement 12 is substantially larger than that of device which do not include sink mechanism 14.

Figure 1B:
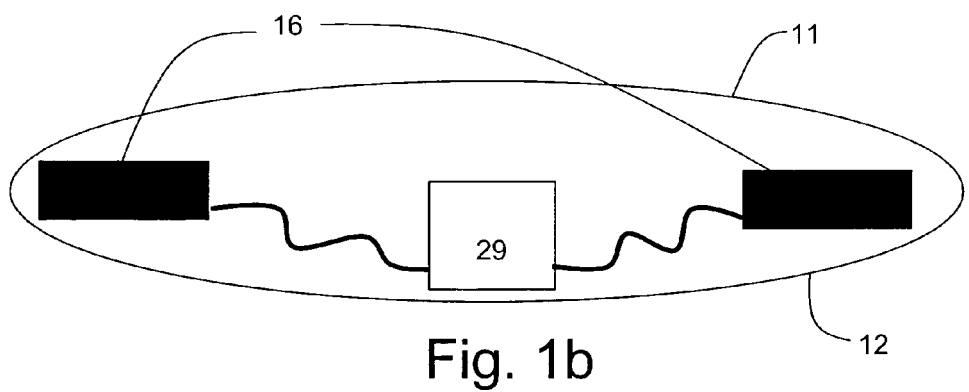
FIG. 1b is a schematic cross-sectional view of a sink device, according to a preferred embodiment of the present invention.

As stated above, sink mechanism 14 may also be embodied as a sink device. Thus, referring to FIG. 1b, according to a preferred embodiment of the present invention, sink mechanism 14 may comprise a power source 29 and electrodes 16 for generating an electric current through the device (hence through constituent-of-interest 15), so as to generate a oxidation-reduction reaction in which constituent 15 is transformed into a non-toxic substance. Power source 29 may also be powered by RF, induction, magnetic or ultrasonic source provided from outside the body and/or controlled by wireless communication using, for example, suitable short distance wireless communication, such as, but not limited to, Bluetooth technology or the wireless communication implemented in the GivenImaging peal.

According to a preferred embodiment of the present invention, device 10 may further comprise a heating mechanism 52 which may be used for generating heat is confinement 12 and/or the surroundings of device 10. Heating mechanism 52 can be utilized to facilitate or catalyze removal of the gastrointestinal constituent. For example, heating mechanism 52 can be used to generate heat which can denature proteinaceous compounds diffusing into confinement 12 through a selective membrane as described hereinabove. The heating is also useful, for example, for dilation of blood vessels deeper than mucosal blood vessels (to generate subsequent hyperemia), or for regulating bowel motility or secretion from internal glands (of the mucosa or even pancreatic endocrine secretions).

Many types of heating mechanisms may be used with the present invention. For example, a miniaturized power source which generates an electrical current within device 10 may be sufficient for heating any of its components, the heating can also be a result of an exothermic chemical reaction. For example, a mixture of magnesium iron alloy and sodium chloride with water generates heat and produces magnesium hydroxide as an end product, while calcium oxide or quicklime produces heat by reacting with water. In addition, polymerization of methyl methacrylate, plastic monomers or polyurethane cqan also be utilized to generate heat since such reactions are exothermic. Local heat induction on the surface of the device (used alone or in combination with other features) can also be used for accelerating enzymatic reactions and for treatment of hypothermia.

According to a preferred embodiment of the present invention, device 10 may further comprise a mixing mechanism 54 for actively mixing a content of confinement 12 and/or the surroundings of the device. A skilled artisan would appreciate that the mixing procedure accelerates the particle exchange between confinement 12 and the gastrointestinal tract (which, as stated, is otherwise statistical in nature, following the laws of thermodynamics), therefore enhances the efficiency of the device. Any mixing mechanism known in the art may be used, such as, but not limited to, a mechanical mixer, a sound wave generator and a heating device, which induces turbulences within confinement 12 or at the periphery and surroundings of device 10.

Figure 3:
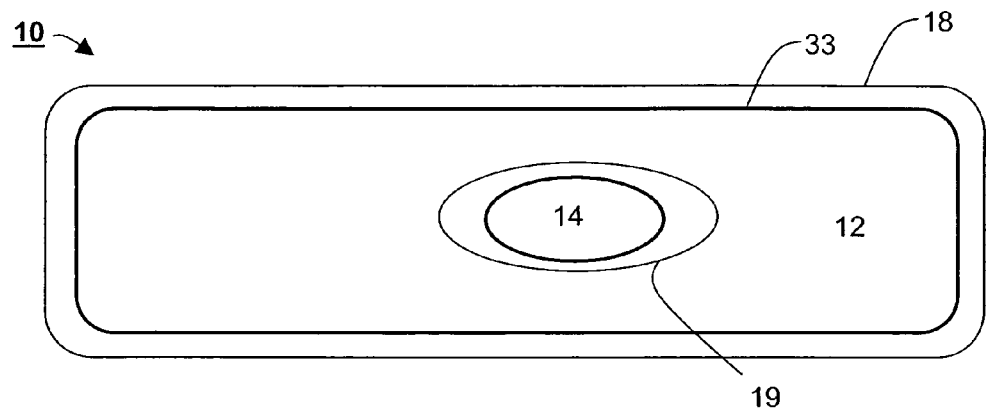
FIG. 3 is a schematic cross-sectional view of an alternative embodiment of the device of FIG. 1a illustrating a housing according to a preferred embodiment of the present invention.
Figure 4:
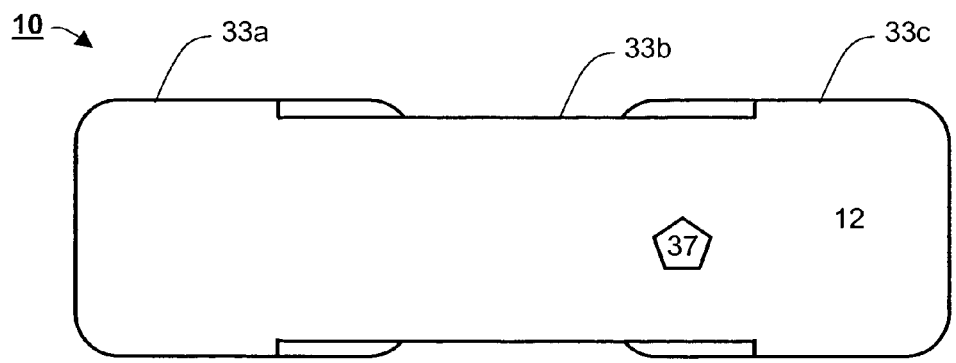
FIG. 4 is a schematic cross-sectional view of an alternative embodiment of the device of FIG. 1a, in which the housing is made expandable, according to a preferred embodiment of the present invention.

Reference is now made to FIGS. 3-4, which is a schematic illustration of device 10 in which confinement mechanism 11 comprise a housing 33, according to a preferred embodiment of the present invention. In this embodiment, device 10 may have a capsule-like shape, as shown, or may have any other shape as desired. Housing 33 may be constructed of a material which is permeable or semi-permeable to bodily fluid, allowing selective entry of constituent 15 into confinement 12 and, at the same time, shielding from various materials which can disrupt or compete for the function of the sink mechanism within device 10, thus facilitating and enhancing the efficiency thereof.

Alternatively, or in addition, device 10 or some of its internal components (e.g., sink mechanism 14) can be encapsulated in a protective cover 19 of a degradable substance, such as similar to an oral medication capsule that is composed of, for example, gelatin, glycerin, egg shell, starch, edible oil, fat or vegetable oil, water soluble fiber or a mixture of these materials. Cover 19 can assure the stability of the material when inserted inside device 10. Once device 10 is ingested, the cover 19 is degraded, thus liberating sink mechanism 14 to interact with the contents of device 10.

The use of cover 19 allows the device of the present invention to carry components which would otherwise be damaged by the harsh conditions, e.g., pH, present in predetermined regions of the gastrointestinal tract, such as the stomach, directing its main action into the small intestine below it. In other cases, the device can be coated with substances that may induce more mucosal permeability like zonulin or other permeation enhancers for more availability of some drugs or bigger molecules (not otherwise passively secreted into the lumen) for its further removal by the sink mechanism. Alternatively, a permeation enhancer, such as zonulin, can be co-administered with the device of the invention.

FIG. 3 also shows a selective membrane 18, which, as stated, is preferably used for preventing constituents other that constituent 15 to enter confinement 12. It is to be understood that although in FIG. 3 membrane 18 externally encapsulates housing 33, other configuration (e.g., internal membrane) are not excluded from the scope of the present invention. In such case, sink mechanism 14 may be linked to a molecule to which the membrane is impermeable, so as to prevent mechanism 14 from escaping device 10. The membrane hence also serves at least in part as confining mechanism 11. In addition, the membrane can confine the sink material that otherwise could be irritant to the intestine mucosa, avoiding complication, but allowing its action over the constituents.

Membrane 18 may also be unilateral membrane to allow net influx of the constituents but prevent efflux thereof. Membrane 18 is preferably able to withstand all physiological temperatures or pH and may have a variable range of porosity. Suitable membranes include dialysis membranes that are typically used in chemistry for separation of substances on suspensions, solutions, columns, tissue cultures, etc. These membranes can be produced from various materials including regenerated cellulose, a mixture of chemically pure cellulosic esters and a polyvinylidine fluoride, which is a flouropolymer, like Teflon™, and is resistant to most organic solvents, as well as, corrosive aqueous solutions. These membranes can also be chosen based on their chemical compatibility such that the membranes are stable in various chemical environments.

Incorporation of a separate membrane 18 can be accomplished in various manners. In one embodiment, membrane 18 is internal and freely moves throughout confinement 12 of device 10. Alternatively, membrane 18 is secured to housing 33 so as to cover openings which may be formed around the periphery or ends of device 10 to allow passage of bodily fluids therethrough. Membrane 18 may be similar to a bag containing a substance inside, or may be one or more pieces of membrane material.

Housing 33 may be hard or semi-flexible, and can be of fixed dimensions or may be selectively expandable in one or more directions. Forming housing 33 of a material so that it can expand to a predetermined desired degree within the gastrointestinal tract during use, has several advantages.

First, it is appreciated that device 10, being designed to be ingested, is favorably compact when the ingestion of the device is prompted. Subsequently, device 10 may be expanded, so as to enlarge the contact area between device 10 and the gastrointestinal fluids, hence to increase the net influx and the device's efficiency.

Second, an expandable device allows more of desired constituents to engage confinement 12 hence increases the number of constituents removed from the body.

Third, when conversion mechanism 16 comprise bacteria (or any other mechanism which experience reproduction or multiplication), it is desired to enlarge the size of confinement 12 so at to allow or encourage the reproduction of the bacteria, thereby to enhance the net influx of constituent 15.

The expansion of housing 33 may be facilitated by its construction. Referring to FIG. 4, according to a preferred embodiment of the present invention housing 33 may be formed from a series of sections formed into a telescoping mechanism, which allows selective expansion of the housing. In such a configuration, housing sections 33a and 33c are telescopically engaged with a central section 33b. In this way, sections 11a and 11c are preferably moveable longitudinally relative to section 33b, for selective expansion of the housing 33. Alternatively, sections 33a and 33c may be interconnected by a central section 33b formed, e.g., in an accordion configuration. Additional structures to allow selective expansion of housing 33 are also contemplated, including folded flexible sections and the like.

According to a preferred embodiment of the present invention housing 33 is designed and constructed so as to prevent damage to the contents of the device (e.g., sink mechanism 14) by constituents of the gastrointestinal tract other than constituent 15. For example, in cases where sink mechanism 14 is sensitive to the harsh environment of the gastrointestinal tract (e.g., low pH), device 10 may also comprise a buffering agent such as or a suitable ion exchanger which can effectively maintain the microenvironment around sink mechanism 14 at a suitable desired pH.

Housing 33 may also serve for preventing damage, such as chemical or physical irritation, to the gastrointestinal tract by sink mechanism 14.

According to a preferred embodiment of the present invention housing 33 is bioresistant. Materials that can be used to form housing 33 of device 10 include, but are not limited to, polyurethane, polystyrene, plastics, polymers, silicon or other synthetic material, new shape memory polymers and metallic materials including, without limiting, stainless steel and Nitinol, which is a shape memory alloy that may be programmed to expand inside the gastrointestinal tract due to a change in body temperature.

While device 10 can have various conventional shapes and sizes, a typical size of housing 33 is about 11 millimeters in diameter and about 30 millimeters long. Device 10 can also be sized to facilitate use with children, or otherwise as desired.

As used herein the term "about" refers to ±10%.

Housing 33 of such or other dimensions may be constructed, for example, from silicone-urethane co-polymers (e.g., PurSil™) or a ceramic multilayer film. The device can be fabricated using vacuum-forming techniques or injection molding, for further information, see, e.g., http://www.polymertech.com/device.html)

Suitable membranes to be used with device 10 include, without limiting, Empore™ products available from 3M Inc. http://www.3m.com/empore/Formats/index.htm). A typical pore size of such membrane is about 1500 Da.

The device of the present invention provides numerous benefits over the simple polymers designed for absorption of gastrointestinal fluid constituents described hereinabove. Use of a selective and optionally unilateral membrane and an internal confinement enables trapping and thus removal of a wide range of substances. In addition, since the confinement of the device is effectively shielded from gastrointestinal fluids it enables removal rather than absorption of the constituents thus minimizing the exposure of the gastrointestinal tract to these constituents. Furthermore, the shielded cavity enables use of agents which would not otherwise function if exposed to the conditions present in the gastrointestinal tract. Finally, combined use of semi-permeable and optionally unilateral membranes and agents enables selective constituent-uptake and as a result reduces the likelihood that a function of the treatment agent is reduced or completely inhibited by gastrointestinal constituents other than the targeted constituent.

In the treatment of patients, it may also be desirable to track device 10 as it passes through the gastrointestinal tract or other portions of the body. Hence, according to a preferred embodiment of the present invention device 10 is made detectable by at least one detection method, preferably non-invasive detection method, such as, but not limited to, x-ray imaging, magnetic resonance imaging, ultrasound imaging, gamma-camera imaging and automatic path/positioning tracking. This may be done by positioning or attaching a detectable tag 37 to device 10.

If desired, tag 37 may also be triggered by certain activity of device 10 within the gastrointestinal tract, such as by reactivity with predetermined constituents, an indication of treatment or treatment progress, or the like. Examples of technologies which can be utilized to track device 10 within the gastrointestinal tract are provided in, for example, U.S. Pat. No. 5,170,801.

Figure 5:
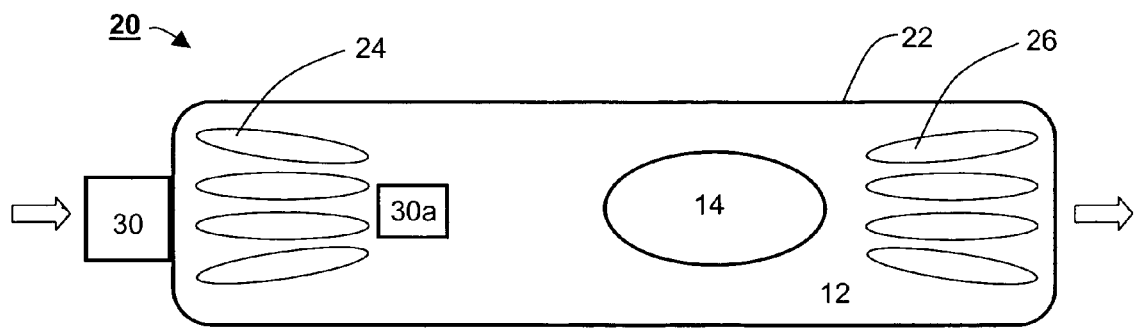
FIG. 5 is a schematic cross-sectional view of an embodiment illustrating use of a pump or motor facilitating the active transmission of fluids through the ingestible device of the present invention.

A further embodiment of the invention is shown in FIG. 5, which is directed to a device 20, capable of actively transmission of bodily fluids therethrough, e.g., using a flow generating mechanism 30. Devise 20 preferably serve a function similar to the embodiments already described above. Device 20 may include a housing 22, which may again be formed of a rigid or semi-flexible shell that can tolerate all physiological degrees of pH or temperature to be encountered within the gastrointestinal tract. In this embodiment, housing 22 may be configured to have an ingress opening 24 and an egress opening 26, which may be disposed on opposing ends of device 20 as shown, or in another suitable fashion for the ingress of bodily fluids into confinement 12 formed by housing 22. For the active transmission of fluids through device 20, flow generating mechanism 30, which may be, e.g., a pump or a motor, located relative to confinement 12 of device 20 actively transmits bodily fluids from one end of device 20 through opening 24 to the other end through opening 26.

The active transmission of bodily fluids with the assistance of transmission mechanism 30 through confinement 12 promotes flow of the bodily fluids to pass through device 20 hence encourages the net influx of the constituent-of-interests into confinement 12.

Mechanism 30 can be located on the periphery of shell 22 of device 20, as shown in FIG. 5, or may be located internal to device 20 as shown at 30a. In this embodiment, mechanism 30 may also provide a force to propel, rotate or otherwise to cause motion of device 20 inside the body to increase tangent and transverse flows of bodily fluids near device 20, hence to substantially increase the net influx of the constituent-of-interest into confinement 12. Alternate locations of mechanism 30 are near opening 24 to increase the flow into confinement 12 and/or opening 26 for the outward flow through device 20.

Figure 6:
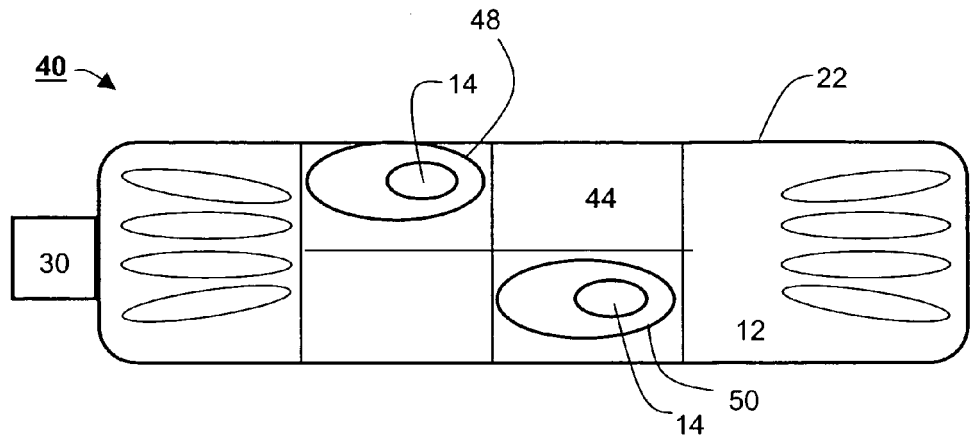
FIG. 6 is a schematic cross-sectional view of an alternative embodiment of the device of FIG. 1a, which comprises multiple compartments, according to a preferred embodiment of the present invention.

Yet another embodiment of the device according to the invention is shown in FIG. 6. This device which is referred to herein as device 40 may have similar characteristics to any of the devices described hereinabove, but may comprise multiple compartments 44 which contain one or more types of sink mechanisms 14. Individual internal membranes 48 may be used with each compartment 44 or a single membrane may be used similarly to that described previously. Alternatively or additionally, degradable encapsulation 50 containing sink mechanisms 14 may be utilized, for releasing sink mechanisms 14 in a predetermined region of the gastrointestinal tract.

The device of the present invention may, if desired, be presented in a pack or dispenser device, such as an FDA approved kit, which may contain one or more units of the device of the present invention. The pack may be accompanied by instructions for administration. The pack may also be accommodated by a notice associated with the container in a form prescribed by a governmental agency regulating the manufacture, use or sale of pharmaceuticals or food supplements, which notice is reflective of approval by the agency of the form of the compositions or human or veterinary administration. Such notice, for example, may be of labeling approved by the U.S. Food and Drug Administration for prescription drugs or food supplements of an approved product insert.

The device can be used to deliver other physical means of treatment or concomitantly to other forms of treatment. That includes radioactive isotopes, cooling, magnetic or electromagnetic fields, electric currents, vibration movements, radio-frequency waves and others that may activate or induce activation of other compounds delivered to the body (through the gastrointestinal tract or any other delivery mode). Examples include, but are not limited to, bone marrow and blood radiation therapy or activation of anti-cancerous drugs, bowel CA, malignant hyperthermia, or stimulation which results from various forms of physical induction (e.g., vertebral bone stimulation in disuse osteoporosis, etc).

Figure 7:
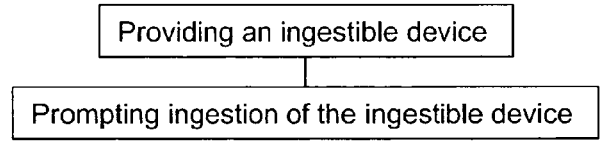
FIG. 7 is a flowchart of a method of using an ingestible device, according to a preferred embodiment of the present invention.

FIG. 7, illustrates, in flowchart format, a method of using ingestible device, such as, but not limited to, devices 10, 20 or 40 of the present invention, where in a first step of the method, the ingestible device is provided and in a second step an ingestion of the device is prompted.

According to another aspect of the present invention there is provided a method of removing or converting at least one constituent-of-interest present in a gastrointestinal tract of an individual.

Figure 8:
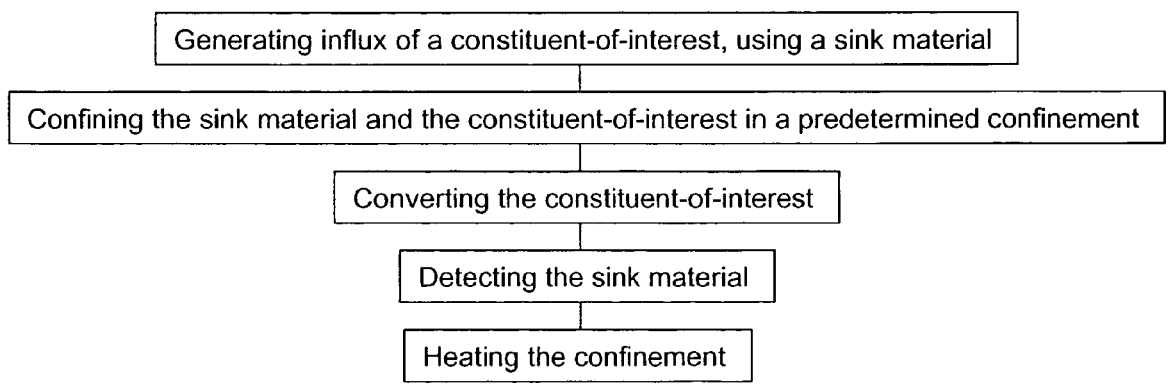
FIG. 8 is a flowchart of a method of removing or converting at least one constituent-of-interest present in a gastrointestinal tract of an individual, according to a preferred embodiment of the present invention.

The method comprises the following method steps which are illustrated in the flowchart of FIG. 8. Hence, in a first step, a net influx of the constituent-of-interest, is generated using a sink mechanism, and in a second step the sink mechanism and the constituent-of-interest are confined in a predetermined confinement. According to a preferred embodiment of the present invention the first and the second steps are performed substantially contemporaneously.

Optionally, the constituent-of-interest may be converted, e.g., using conversion mechanism as further detailed herein above. Other optional method steps include detecting of the sink mechanism and heating the confinement and/or the surroundings of the device, as is further detailed hereinabove.

It is expected that during the life of this patent many relevant sink mechanisms will be developed and the scope of the term sink mechanisms is intended to include all such new technologies a priori.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which, together with the above descriptions, illustrate the invention in a non limiting fashion.

The devices and methods, according to preferred embodiments of the present invention operate within the gastrointestinal (GI) and remove undesired highly concentrated intestinal or blood substances or metabolites, and hence such devices would be suitable for treating numerous disorders. The removal of various substances from gastrointestinal fluids using one or more devices provides an alternative to conventional treatments.

As described hereinabove, effective removal of unwanted GI substances is facilitated by a device-integrated sink mechanism, which is preferably designed capable of specifically removing one or more GI substances.

Following are several examples of disorders and symptoms that can be treated by the device of the present invention.

Treatment of Poisoning:

According to a preferred embodiment of the present invention the device of the present invention is used to treat poisoning.

In this embodiment, the device is filled with suitable chelator including resins such as Lewatit resins or AMBERLITE™ (Sybron Chemicals Inc. a Bayer Company). Ion Exchange Resins (Rohm and Haas) is first used to generate net influx of a toxic compound (such as, but not limited to, lead, mercury, cadmium aluminum and arsenic), and then to ionize the toxic compound. According to a preferred embodiment of the present invention the device both separates the toxic compound from GI fluids, by the aforementioned influx, as well as converts it to a less toxic state. Other chelator agents that may be used in this embodiment include, without limitation, EDTA, Dimercaptol (BAL), DMSA, and D-penicillamine. Natural materials, such as, but not limited to, phytochelatines (vegetal heavy metal chelatoors), algae (e.g. alginate), vegetal fibers (e.g. Psyllium), clays, or other natural extracts alone or in combination, may also be used to absorb certain heavy metal ions.

An example of such a material is a composite biosorbent prepared by coating chitosan (obtained by deacetylation of chitin, extracted from the shells of shrimps, crabs, and other crustaceans, insects, and fungi) onto ceramic alumina. One ordinarily skilled in the art will appreciate that such material is suitable for chelating lead, mercury, cadmium, chromium and nickel.

Absorption and/or Ionization of Compounds Associated with Specific Disorders:

According to a preferred embodiment of the present invention, the device can be utilized to reduce excessive levels of compounds which are specifically associated with certain types of disorders. In this embodiment, the device preferably comprises an ion exchange resin or a chelator agent, which are useful for reducing high levels of ammonia associated with liver and renal failure, high levels of potassium associated with hyperkalemia, cooper which its presence is indicative for Wilson's disease and excess levels of iron characterizing hemochromatosis and hemosiderosis.

Treatment of Renovascular Hypertension:

According to a preferred embodiment of the present invention the device can be utilized to treat individuals having renovascular hypertension.

Renovascular hypertension is caused by narrowing of the arteries that carry blood to the kidneys. Renovascular hypertension is a form of secondary hypertension occurring in less than 5% of all people with hypertension and characterized by narrowing of the renal artery leading to reduced blood flow to the kidney. Symptoms usually begin before age 30 or after age 50, depending on the cause of the damage to the kidney blood vessels. Stenosis is often related to atherosclerosis but may be caused by injury to the artery that causes scarring. Reduced blood flow to the kidney leads to an excessive release of the hormone renin, a potent hormone that increases blood pressure by activating the production of angiotensin II. Thus, according to a preferred embodiment of the present invention the device is designed for removing angiotensin II from gastrointestinal fluids. One of ordinary skill in the art will appreciate that with such configuration, the device can be used to reduce symptoms of renovascular hypertension due to reduced levels of angiotensin II in the gastrointestinal fluids.

For treatment of renovascular hypertension, the device of the present invention preferably comprise antibody molecules (polyclonal, monoclonal or antibody fragments, e.g., Fab, ScFv, etc.), capable of specifically binding angiotensin II. Such antibody molecules can be introduced in more than one way.

Hence, in one embodiment, the antibody molecules are attached to particles (e.g., polystyrene beads) which are trapped within the device. In another embodiment, the antibody molecules are attached directly or indirectly (via a linker) to the wall lining the housing of the device. In an additional embodiment, the antibody molecules are left soluble within the device. In any event, the density of the antibody molecules is preferably selected so as to allow efficient trapping of angiotensin II molecules within the device while at the same time not substantially hindering diffusion of gastrointestinal fluids and small molecules through the device. Since some antibody-antigen reactions are controlled by pH and ion concentration, the device can also comprise ion exchange resins and buffers capable of maintaining the pH within the device at an optimum for binding (for additional information, see, e.g., http://www.rohmhaas.com/ionexchange/). The antibody utilized by the device of the present invention can be generated according to the teachings of Dagenais and Escher (E. Regul Pept. 1993 Mar. 19;44(2): 239-47) or commercially purchased from IBL (Hamburg, Germany http://www.ibl-hamburg.com).

Treatment or Renal or Prerenal Failure:

According to a preferred embodiment of the present invention can be utilized to treat individuals having renal or prerenal failure.

Renal or prerenal failure is typically accompanied by existence of high levels of $NH_3$, urea and creatinine in the blood. The removal of these materials by the devices and methods of the present invention may be an adequate substation to the need of dialysis. Thus, the device of the present invention is preferably designed suitable for removing $NH_3$, urea and creatinine from gastrointestinal fluids.

For treatment of renal or prerenal failure, the device of the present invention can include a conversion mechanism of ion exchange resin, capable of converting $NH_3$ to $NH_4$ by ionization. The urea and the creatinine may be entrapped within the confinement of the device (e.g., using a unilateral membrane) to be removed from the body through peristaltic motion of the gastrointestinal tract. Suitable sink mechanism for the designed device, includes natural or synthetic Zeolites, Dowex resins produced by Dow Chemical or chitosan-coated dialdehyde cellulose (chitosan DAC) for generating net influx of $NH_3$, urea and/or creatinine, respectively. In addition, activated charcoal or other sorbents like AST-120 (porous spherical carbonaceous material) can be utilized.

Treatment of Intestinal Enzymatic Deficiencies:

According to a preferred embodiment of the present invention the device is designed for mobilizing enzymes to the gastrointestinal tract and thus can be utilized to treat individuals having certain enzymatic deficiencies such as lactase, sucrase, and maltase that degrade the corresponding disaccharides, lactose, sucrose, and maltose into their monosaccharide components.

For treatment of the aforementioned enzyme deficiencies, the sink mechanism of the device can include the immobilized enzyme (e.g., lactase), capable of degrading the disaccharides (e.g., lactose) in the intestinal tract thus, avoiding its accumulation that may lead to diarrhea and abdominal distention. Appropriate pH conditions for the enzyme optimal activity in the device can be assured using appropriate buffers.

Treatment of Interleukin-6 Associated Disease:

According to a preferred embodiment of the present invention the device is designed for removing of Interleukin-6 (IL-6) and thus can be utilized to treat individuals having diseases associated with its presence in the intestines.

IL-6 is thought to contribute to the pathogenesis of many diseases, including rheumatoid arthritis and inflammatory bowel disease. It is present in very high levels in both serum and intestinal tissue of patients with Crohn's disease. Other conditions such as multiple myeloma, and a malignant tumor of the bone marrow, are accompanied by its excess/presence.

For treatment of the aforementioned diseases, the sink mechanism of the device can include immobilized IL-6 antibody molecules or bacteria genetically modified capable of synthesizing IL-6 antibodies.

Treatment of TNF Associated Disease:

According to a preferred embodiment of the present invention the device is designed for removing Tumor Necrosis Factor α (TNFα) and thus can be utilized to treat individuals having diseases associated with its presence in the intestines.

TNFα elevated levels in stool samples have been shown in patients with inflammatory bowel disease. Other clinical conditions such as psoriasis, rheumatoid arthritis, and asthma are typically accompanied by excess/presence of TNF.

For treatment of the aforementioned diseases, the sink mechanism of the device can include immobilized TNFα antibody molecules or bacteria genetically modified capable of synthesizing TNFα antibodies.

Treatment of Acute Lymphocytic Leukemia:

According to a preferred embodiment of the present invention the device can also be designed for removing L-asparagine and thus can be utilized to treat individuals having Acute Lymphocytic Leukemia (ALL).

ALL (also known as acute lymphoid leukemia and acute lymphoblastic leukemia), is the most common type of leukemia under the age of 19. ALL results from an acquired genetic injury to the DNA of a single cell in the bone marrow. The effects of ALL are uncontrolled and exaggerated growth and accumulation of lymphoblasts, which fail to function as normal blood cells, and blockade of the production of normal marrow cells, leading to a deficiency of red cells, platelets and normal white cells in the blood. The tumor cells of ALL patients are unable to synthesize the normally non-essential amino acid L-asparagine; therefore, they are forced to extract it from body fluids to survive.

For treatment of ALL, the sink mechanism of the device can include immobilized L-asparagine antibody molecules or an enzyme capable of L-asparagine degradation such as asparaginase in order to reduce the free exogenous concentration of L-asparagine without affecting the function of normal cells.

Treatment of Gout:

According to a preferred embodiment of the present invention the device is designed for oxidizing urate and thus can be utilized to treat individuals having gout disease.

Gout is a painful rheumatic disease, resulting from deposits of needle-like crystals of uric acid in connective tissue, and/or in the joint space between two bones. These deposits lead to inflammatory arthritis, which causes swelling, redness, heat, pain, and stiffness in the joints. Gout accounts for approximately 5% of all cases of arthritis. Uric acid is a substance that results from the breakdown of purines, which are part of all human tissue and are found in many foods. Normally, uric acid is dissolved in the blood and passed through the kidneys into the urine, where it is eliminated. If the body increases its production of uric acid or if the kidneys do not eliminate enough uric acid from the body, it is accumulated in the blood (a condition called hyperuricemia). Deposits of uric acid, called tophi (singular: tophus), can appear as lumps under the skin around the joints and at the rim of the ear. In addition, uric acid crystals accumulated in the kidneys and cause kidney stones.

For treatment of gout, the sink mechanism of the device of the present invention can include an immobilized enzyme capable of oxidizing urate (such as, urate oxidase or uricase) in order to reduce the level of uric acid.

Treatment of Hypercholesterolemia:

According to a preferred embodiment of the present invention the device is designed for removing cholesterol from gastrointestinal fluids and the blood circulation surrounding the gastrointestinal tract and thus can be utilized to treat individuals having hypercholesterolemia.

Hypercholesterolemia is a condition characterized by high levels of cholesterol in the blood. While cholesterol is an essential part of a healthy body, high levels thereof increase a risk for cardiovascular disease, which can lead to stroke or heart attack. Excess level of cholesterol circulating in the blood can create plaque along the artery walls, which plaque eventually obstruct or even block the flow of blood.

Thus, for treatment of hypercholesterolemia, the sink mechanism of the device of the present invention can include a bile acid binding resin or an agent capable of synthesizing the cholesterol into long fat chains, such as, Cholestyramine (Duolite AP) in order to reduce cholesterol levels in the blood.

Reducing Absorbance of Undesired Molecules:

According to a preferred embodiment of the present invention the device can also be designed for reducing the absorbance of undesired molecules from the gastrointestinal fluids and thus can be utilized to treat individuals having diverse conditions limiting their diet.

Certain conditions require an individual to avoid or reduce specific food components from his normal diet such as low glucose diet for diabetes, low sodium diet for hypertensive patients, and low fat and carbohydrate for obese patients. The carbohydrates are absorbed in the intestines as single glucose molecules after breakage of polysaccharide chains. Lipids are absorbed as fatty acids, cholesterol and monoglycerides after emulsification and dissolution in the aqueous media of the intestinal lumen in the presence of bile salts. The size of the fat globules is the limiting factor in its absorption. Before emulsification by bile salts, lipid globules have an average diameter of 100 nm, while afterwards their diameter is reduced to 5 nm.

Thus, for reducing absorbance of undesired molecules, the sink mechanism of the device of the present invention preferably includes enzymes capable of synthesis of polysaccharides from single glucose molecules or conjugation of fatty acids to form bigger fat globules for avoidance of normal absorption and reducing their concentration in the enterocytes and subsequent levels in blood. Alternatively, chitosan can be used as an effective adsorbent for removing free fatty acids. Other embodiments include, without limitation, exchange resins for sodium trapping or specific antibodies for known food allergens.

In the specific case of sprue or celiac disease, where there is an immunological response to gliadin, present in the gluten of certain types of food, the device of the present invention preferably comprises immobilized gliadin antibody molecules or bacteria genetically modified capable of synthesizing gliadin antibodies.

Reducing Alcohol and Acetaldehyde Ingestion:

According to a preferred embodiment of the present invention the device is designed for reducing the levels of alcohol and acetaldehyde and thus can be utilized to reduce damaging effects of alcohol consumption.

In humans, ethanol is converted to acetaldehyde by alcohol dehydrogenase (ADH), followed by its oxidation to a less harmful molecule-acetate, by aldehyde dehydrogenase (ALDH). Acetaldehyde is a toxic metabolite that is responsible for the hepatic damage and risk factor for alimentary tract cancers.

Thus, for reducing alcohol and its degradation products levels, the sink mechanism of the device of the present invention preferably comprises immobilized ALDH enzyme for oxidation of endogenous (bacterial produced) acetaldehyde and the one resulted from the ingested ethanol metabolism. The sink mechanism may also comprise immobilized ADH enzyme in addition to ALDH, for conversion of ethanol and acetaldehyde in one device. Other resins capable of absorbance of organic materials like alcohols (e.g. Tenax, TA) may be included in the device as a sink mechanism suitable for ethanol, methanol and aldehydes.

Treatment of Phenylketonuria:

According to a preferred embodiment of the present invention the device is designed for mobilizing phenylalanine hydroxylase to the gastrointestinal tract and thus can be utilized to treat individuals having Phenylketonuria (PKU).

PKU is an inherited error of metabolism caused by a deficiency in the enzyme phenylalanine hydroxylase. The absence of this enzyme results in mental retardation, organ damage, unusual posture and in cases of maternal PKU it can severely compromise pregnancy. Classical PKU is an autosomal recessive disorder, caused by mutations in both alleles of the gene for phenylalanine hydroxylase, found on chromosome 12. Phenylalanine hydroxylase converts the amino acid phenylalanine to tyrosine. Mutations in both copies of the gene for this enzyme, leads to inactive or less efficient enzyme thus, the concentration of phenylalanine in the body can build up to toxic levels.

Thus, for treatment of PKU, the sink mechanism of the device of the present invention preferably comprises a cofactor capable of performing phenylalanine enzymatic hydroxylation, such as, tetrahydrobiopterin. The sink mechanism may comprise antibodies, chelators, and/or enzymatic transformation directed toward aspartame or its metabolites. Aspartame (an artificial sweetener widely used in the food industry), contraindicated in PKU patients, due to produce phenylalanine as a by product, therefore its reduction or conversion is expected to reduce or eliminate its effects on PKU patients.

Treatment of Hydroxytryptamine Associated Diseases:

According to a preferred embodiment of the present invention the device is designed for removing Hydroxytryptamine (5-HT or serotonin) and thus can be utilized to treat individuals having diseases associated with its presence in the intestines.

Hydroxytryptamine (5-HT or serotonin) is a compound found in intestinal secretions and when it is released, it activates 5-HT receptors on mucosal vagal afferent terminals. Thus, 5-HT acts as a paracrine substance to stimulate pancreatic secretion via a vagal cholinergic pathway. 5-HT was suggested to have a role in Irritable Colon syndrome as well as Carcinoid Syndrome.

Thus, for reducing serotonin levels, therefore treating the aforementioned syndromes, the sink mechanism of the device preferably comprises immobilized serotonin antibody molecules or bacteria genetically modified capable of synthesizing serotonin antibodies, or alternatively, an enzyme capable of serotonin conversion.

Treatment of Substance-P Associated Diseases:

According to a preferred embodiment of the present invention the is designed for reducing substance-P and thus can be utilized to treat individuals having diseases associated with its presence or high levels.

High level of substance-P in the blood is a recognized indication of many disorders, such as chronic pain, fibromyalgia and depression. There is evidence of presence and localization of substance-P receptors on epithelial cells of the normal small and large intestine. Up-regulation of expression of such receptors was shown in disorders such as Crohn's disease and ulcerative colitis.

Thus, for treating the aforementioned diseases the sink mechanism of the device preferably comprises immobilized substance-P antibody molecules or bacteria genetically modified capable of synthesizing substance-P antibodies. Optionally and preferably, the sink mechanism of the device comprises bacteria genetically modified capable of synthesis of such antibodies.

Reduction of Intestinal Permeability Resulted by Various Conditions:

According to a preferred embodiment of the present invention the device is designed for reducing Zot and/or zonulin and thus can be utilized to treat individuals having diseases associated with the presence or high levels of these toxins.

Intestinal permeability is altered in inflammatory bowel diseases, enteral bacterium, and parasite infections, as a result of certain drug intake, food allergies or intoxication by toxins, major trauma and burns or celiac disease. This increased intestinal permeability leads to severe diarrhea, increased intestinal secretions, while allowing unwanted substances to cross the intestinal barrier. The pathogenesis of this condition, involves the presence of Zonula occludens toxin (Zot), or up-regulation of zonulin, its eukaryotic analogue, that reversibly open the intestinal tight junctions between the cells of the intestinal epithelium (enterocytes).

Thus, for treating the aforementioned conditions the sink mechanism of the device of the present invention preferably comprises immobilized an anti-Zot and/or anti Zonulin antibodies or bacteria genetically modified capable of synthesizing such antibodies, or alternatively, an agent capable of inhibiting the action of these molecules (Zot and zonulin) through the sink mechanism.

Reduction or Eliminations of Undesired Drugs:

According to a preferred embodiment of the present invention the device is designed for reducing specific drugs and thus can be utilized in cases such as drug overdoses, when the drug is not longer needed or when is producing unwanted side effects.

Thus, for treating lithium poisoning, the sink mechanism of the device of the present invention preferably comprises natural Bentonite mineral (clay) or synthetic resin.

Drugs that enter the entero-hepatic circulation can also be recovered with the specific sink mechanism suitable for each case, using antibodies, chelators or transforming agents. Taking advantage of the modulation of intestinal permeability using coated devices of the present invention with modulator agents, the levels of an extended range of large molecule drugs and other substances can be reduced through a suitable sink mechanism.

A summary of the aforementioned examples and others is provided in Table 1, below.

TABLE 1

| | | Conversion Mechanism | | |
| --- | --- | --- | --- | --- |
| Disorder | Constituent | Chemical | Physical | Enzymatic |
| Renal or prerenal failure | $NH_3$ | | Ionization to produce $NH_4$ | |
| Renal or prerenal failure | Urea and Creatinine | | Entrapping | |
| Chronic pain | Substance-P | Substance-P Antibody | | Bacterial synthesis of antibodies |
| Fibromyalgia | Substance-P | Substance-P Antibody | | Bacterial synthesis of antibodies |

TABLE 1-continued

| Disorder | Constituent | Conversion Mechanism | | |
|---|---|---|---|---|
| | | Chemical | Physical | Enzymatic |
| Depression | Substance-P | Substance-P Antibody | | Bacterial synthesis of antibodies |
| Gout | Uric acid | | | Oxidation of urate |
| NIDDM | Glucose (Glu) Disaccharides | Glu or Disaccharide Antibody | | 1. Synthesis of polysaccharide 2. Degradation of glucose |
| Liver failure | Ammonia | | ion-exchange resin | |
| Hyperkalemia | Potassium | | ion-exchange resin | |
| Lead intoxication | Lead | | ion-exchange resin | |
| Wilson's Disease | Cooper | | ion-exchange resin | |
| Mercury intoxication | Mercury | | ion-exchange resin | |
| Cadmium intoxication | Cadmium | | ion-exchange resin | |
| Aluminum intoxication | Aluminum | | ion-exchange resin | |
| Hemochromatosis Hemosiderosis | Iron | | ion-exchange resin | |
| Arsenic poisoning | Arsenic | | ion-exchange resin | |
| Obesity | Glucose Disaccharides Free fatty acid cholesterol | | | 1. Synthesis of polysaccharide 2. free fatty acid conjugation |
| Carcinoid | serotonin | serotonin Antibody | | |
| Hyper cholesterolemia | Cholesterol | | Bile acid binding resin | Synthesis of long fat chains |
| Rheumatoid Arthritis | TNF | TNF Antibody | | |
| Celiac disease, Sprue | Gliadin, gluten | Gliadin Antibody | | Bacterial synthesis of antibodies |
| Inflammatory bowel disease | Zot Zonulin | Zot and/or zonulin antibody | | Bacterial synthesis of antibodies |
| Multiple Myeloma | Interleukin-6 (IL-6) | IL-6 Antibody | | Bacterial synthesis of antibodies |
| Anemia (macrocytic) | Gut substrates | | | Bacterial synthesis of Folic acid and/or B12 |
| Phenylketonuria | phenylalanine | | | Phenylalanine enzymatic hydroxylation |
| Maple Syrup Urine Disease | alpha-ketoacids | | | Enzymatic breakdown: dehydrogenation |
| Endocrine paraneoplasic Synd | Specific excess hormones | Specific Antibodies | | Bacterial synthesis of antibodies |
| Asthma | TNF | TNF Antibody | | Bacterial synthesis of antibodies |
| Psoriasis | TNF | TNF Antibody | | Bacterial synthesis of antibodies |
| Migraine | Serotonin (5HT) | 5HT Antibody | | Bacterial synthesis of antibodies |
| Ethanol intoxication | Ethanol Acetaldehyde | | | Enzymatic breakdown |
| Acute Lymphocytic leukemia | L-asparagine | L-asparagine Antibody | | L-asparagine degradation |

TABLE 1-continued

| Disorder | Constituent | Conversion Mechanism | | |
|---|---|---|---|---|
| | | Chemical | Physical | Enzymatic |
| Drugs overuse | Specific drugs | Specific drugs antibodies | | |
| Adjuvant therapy of various Tumors | Tumor products | Specific Antibody | | 1. Bacterial synthesis of antitumoral enzymes and/or factors 2. enzymatic degradation of tumor products |
| Immune deficient status | Various antigens | | | Passive immunity: Bacterial synthesis of antibodies |

Packaging the Device:

Any of the device types of the present invention described hereinabove can be packaged and identified for use in treating specific diseases and conditions. Such description can be provided by an informative leaflet packaged along with the device or printed on the packaging material. In any case, such information would preferably also include type and composition of sink mechanism, directions for use, side effects, if any, and any related information which can facilitate effective use of the device.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An ingestible device, comprising:
   (a) a sink mechanism for generating a net influx of at least one constituent-of-interest present in a gastrointestinal tract of an individual such that said at least one constituent-of-interest becomes absorbed in said sink mechanism; and
   (b) an outer housing comprising a confining mechanism for confining said sink mechanism inside said housing in a predetermined confinement, hence directing said net influx is into said confinement.

2. The device of claim 1, wherein said net influx generated by said sink mechanism is substantially higher than a net influx generated by a concentration difference of said at least one constituent-of-interest devoid of said sink mechanism, said concentration difference being the difference between concentrations of said at least one constituent-of-interest in and out of said predetermined confinement.

3. The device of claim 1, further comprising a mixing mechanism for actively mixing a content of said predetermined confinement and/or the surroundings of the device.

4. The device of claim 3, wherein said mixing mechanism comprises a heating device.

5. The device of claim 3, wherein said mixing mechanism comprises a mechanical mixer and a power source for operating said mixer.

6. The device of claim 3, wherein said mixing mechanism comprises a sound wave generator.

7. The device of claim 1, further comprising a flow generating mechanism for actively generating a flow of gastrointestinal fluids through said predetermined confinement.

8. The device of claim 7, wherein said flow generating device is a pump.

9. The device of claim 1, wherein said confining mechanism comprises a housing.

10. The device of claim 9, wherein said housing is composed of a bioresistant material.

11. The device of claim 9, wherein said housing is designed and constructed so as to prevent damage to said sink mechanism by constituents of said gastrointestinal tract.

12. The device of claim 9, wherein said housing is designed and constructed so as to prevent damage to said gastrointestinal tract by the sink mechanism.

13. The device of claim 9, wherein said housing is configured for expanding and/or contracting.

14. The device of claim 1, wherein said confining mechanism comprises linkers linking among molecules of said sink material, thereby forming a molecular mesh structure.

15. The device of claim 1, further comprising a substance for maintaining a predetermined pH level within said predetermined confinement.

16. The device of claim 1, made detectable by at least one detection method for detecting the device in said gastrointestinal tract.

17. The device of claim 16, wherein said at least one detection method is non-invasive.

18. The device of claim 16, wherein said at least one detection method is imaging.

19. The device of claim 16, wherein said at least one detection method is selected from the group consisting of x-ray imaging, magnetic resonance imaging, ultrasound imaging, gamma-gamma imaging and automatic tracking.

20. The device of claim 1, further comprising a protective cover made of a biodegradable material, said protective cover being designed and constructed to degrade only when arriving to a predetermined location of said gastrointestinal tract.

21. The device of claim 1, wherein said at least one constituent-of-interest is selected from the group consisting of a toxin, creatinine, uric acid, a hepatic toxic metabolite, alcohol, an alcohol metabolite, an electrolyte, a therapeutic or a medicinal agent, a detergent, a renal metabolite, a poisonous substance, a nutritional substance, a biochemical compound and a heavy metal.

22. An ingestible device comprising:
(a) a sink mechanism for generating an net influx of at least one constituent-of-interest present in a gastrointestinal tract of an individual; and
(b) an outer housing comprising a confining mechanism for confining said sink mechanism inside said housing in a predetermined confinement, hence directing said net influx is into said confinement, wherein said sink mechanism is selected from the group consisting of a sink material and a sink device, wherein said sink material is for absorbing said at least one constituent-of-interest, wherein said sink material is selected from the group consisting of a high affinity sink material, a low affinity sink material and a combination of a high affinity sink material and a low affinity sink material, and wherein said high affinity sink material is selected from the group consisting of an antibody, whereby said constituent-of-interest is an antigen, a receptor whereby said constituent-of-interest is a ligand, a ligand whereby said constituent-of-interest is a receptor, an enzyme whereby said constituent-of-interest is an inhibitor, an inhibitor whereby said constituent-of-interest is an enzyme and a lectin whereby said constituent-of-interest is a saccharide.

23. The device of claim 22, wherein said low affinity sink material is selected from the group consisting of a nutritional fiber, a clay and a resin.

24. The device of claim 22, wherein at least a portion of said sink material is attached to a solid phase.

25. The device of claim 22, wherein said sink material is water soluble.

26. The device of claim 22, wherein said sink material is water non-soluble.

27. The device of claim 22, wherein said sink material comprises beads.

28. The device of claim 22, wherein said sink material comprises a polymer.

29. The device of claim 22, wherein said sink material comprises an inert solid phase to which affinity sink molecules are attached.

30. The device of claim 22, wherein said sink material is for converting said at least one constituent-of-interest.

31. The device of claim 30, wherein said sink material is a catalyst.

32. The device of claim 31, wherein said catalyst is water soluble.

33. The device of claim 31, wherein said catalyst is attached to a solid phase.

34. The device of claim 30, wherein said sink material is a living organism.

35. The device of claim 34, wherein said living organism is selected from the group consisting of a bacterium, a unicellular parasite, a multicellular parasite and a fungus.

36. The device of claim 35, wherein said fungus is a yeast.

37. The device of claim 34, further comprising a selective membrane for allowing a preferred influx of said at least one constituent-of-interest.

38. An ingestible device comprising:
(a) a sink mechanism for generating an net influx of at least one constituent-of-interest present in a gastrointestinal tract of an individual; and
(b) an outer housing comprising a confining mechanism for confining said sink mechanism inside said housing in a predetermined confinement, hence directing said net influx is into said confinement, wherein said sink mechanism is selected from the group consisting of a sink material and a sink device, wherein said sink mechanism is for converting said at least one constituent-of-interest.

* * * * *